United States Patent
Milla et al.

(10) Patent No.: US 8,820,225 B2
(45) Date of Patent: *Sep. 2, 2014

(54) APPARATUS AND METHOD FOR SENSING AND CONTROLLING THE CONCENTRATION OF PULP IN A CONCENTRATED PULP STREAM

(75) Inventors: Jose D. Milla, Lakeland, FL (US); Gregory W. Schrader, Lakeland, FL (US); Michael L. Suter, Lakeland, FL (US); David S. Danner, Land O Lakes, FL (US)

(73) Assignee: John Bean Technologies Corporation, Chicago, IL (US)

( * ) Notice: Subject to any disclaimer, the term of this patent is extended or adjusted under 35 U.S.C. 154(b) by 162 days.

This patent is subject to a terminal disclaimer.

(21) Appl. No.: 12/840,640

(22) Filed: Jul. 21, 2010

(65) Prior Publication Data
US 2012/0021098 A1 Jan. 26, 2012

(51) Int. Cl.
| | | |
|---|---|---|
| *A23L 2/04* | (2006.01) | |
| *A23L 2/08* | (2006.01) | |
| *G01F 1/00* | (2006.01) | |
| *G01N 9/26* | (2006.01) | |

(52) U.S. Cl.
CPC ... *A23L 2/08* (2013.01); *G01F 1/00* (2013.01); *G01N 9/26* (2013.01)
USPC .................................. 99/486; 99/495; 99/510

(58) Field of Classification Search
USPC ........... 99/231, 232, 307, 321, 489, 495, 519, 99/521, 665; 426/486, 495, 510, 513; 73/73, 863.81
See application file for complete search history.

(56) References Cited

U.S. PATENT DOCUMENTS

| | | | | |
|---|---|---|---|---|
| 2,626,627 | A | * | 1/1953 | Jung et al. ..................... 137/88 |
| 3,898,124 | A | * | 8/1975 | Olson .......................... 162/238 |
| 3,952,577 | A | * | 4/1976 | Hayes et al. ................. 73/54.04 |
| 4,374,865 | A | | 2/1983 | Strobel ......................... 426/599 |
| 4,450,712 | A | * | 5/1984 | O'Shaughnessy ........... 73/61.78 |
| 4,463,025 | A | | 7/1984 | Strobel ......................... 426/599 |
| 4,569,853 | A | | 2/1986 | Strobel ......................... 426/599 |
| 5,260,086 | A | | 11/1993 | Downton et al. ............. 426/599 |
| 5,532,593 | A | * | 7/1996 | Maneval et al. .............. 324/306 |
| 5,992,311 | A | | 11/1999 | Suter et al. ...................... 100/37 |
| 6,375,996 | B1 | * | 4/2002 | Suter et al. ................... 426/231 |
| 6,906,172 | B2 | | 6/2005 | Bratcher et al. |
| 2005/0086994 | A1 | * | 4/2005 | Silvis et al. .................... 73/1.16 |
| 2008/0047973 | A1 | | 2/2008 | Elsom et al. .................... 222/57 |
| 2008/0081094 | A1 | | 4/2008 | Yokoo et al. ................. 426/106 |

OTHER PUBLICATIONS

IMPI Search Report mailed May 12, 2014, issued in corresponding Mexican Application No. MX/a/2013/000782, filed Jul. 19, 2011, 3 pages.

* cited by examiner

*Primary Examiner* — Thien S Tran
(74) *Attorney, Agent, or Firm* — Christensen O'Connor Johnson Kindess PLLC

(57) ABSTRACT

A juice processing apparatus includes a concentrator for generating at least one concentrated pulp stream, and a pulp pasteurizer coupled downstream from the concentrator. A flow restrictor is coupled in the at least one concentrated pulp stream for generating a pressure drop therein. The pressure drop is indicative of a concentration of pulp in the at least one concentrated pulp stream. At least one pressure sensor is associated with the flow restrictor for sensing the pressure drop. A controller is for controlling the concentrator based upon the sensed pressure drop.

20 Claims, 4 Drawing Sheets

APPARATUS AND METHOD FOR SENSING AND CONTROLLING THE CONCENTRATION OF PULP IN A CONCENTRATED PULP STREAM

FIELD OF THE INVENTION

The present invention relates to the field of fruit and vegetable processing, and more particularly, to a juice processing apparatus and method.

BACKGROUND OF THE INVENTION

The juice extraction process is well known to those skilled in the art, such as described in U.S. Pat. No. 5,992,311, assigned to the present assignee, the disclosure of which is hereby incorporated by reference in its entirety. A fruit, vegetable and the like is fed to a juice extractor, which acts as the primary extractor, and produces a pure liquid (juice) and a fibrous material (pulp) from fruit, vegetables and the like.

After extraction, the mixture of juice and pulp is fed as a stream into a pulp concentrator, which is designed to separate a substantial amount of juice from the pulp and to adjust the concentration, or dryness, of the pulp to a desired range. The pulp concentrator may consist of a finisher, which may include a screw type finisher, paddle type finisher, centrifugal type finisher or decanter. The pulp concentrator may also consist of a rotary screen, vibrating screen or other type of separating device as readily appreciated by those skilled in the art.

The screw type and paddle type finishers, for example, rely on the juice to be extruded through a screen material, which regulates the size of the pulp that is maintained within the juice stream. Any pulp that is too large to be extruded through this screen is compressed by centrifugal and mechanical force, which is created by limiting the flow of pulp discharge either by a back pressure regulator and/or a weighted gate.

The juice that is separated from the pulp concentrator is further processed by pasteurization or evaporation as readily appreciated by those skilled in the art. The pulp that is separated from the pulp concentrator has various uses. In some juice processing facilities, this pulp is considered waste or is added to other fruit waste and processed into animal feed. In other juice processing facilities, this pulp is considered a valuable by-product and can either be used for pulpwash or collected as pulp cells. When used for pulpwash, the pulp is washed with water to recover juice solids, such as natural sugars, that are present in the pulp. When collected as pulp cells, the pulp from the concentrator is typically pasteurized to reduce the amount of natural occurring microorganisms prior to packaging, storage or use. Pulp cells may be added back to juice or used as an ingredient in other foods or beverages. When pasteurizing pulp, it is critical to maintain the concentration, or density, of the pulp during pasteurization.

Problems arise, for example, when a pulp pasteurizer is fed with a concentration of pulp less than optimum. The energy for both heating and cooling is increased on a per ton basis of processed material discharged by the pulp pasteurizer in the form of packaged pulp material. Besides having a higher energy cost to produce the product, the final product can be out of density specification. This can result in a loss of product or an increase in reprocessing costs.

When the pulp density is below specification, there is an increase in the amount of carrier juice. Carrier juice is pasteurized along with the pulp and returned to the primary juice stream. Because it is pasteurized along with the pulp, it is often "overpasteurized" leading to quality and organoleptic degradation of the juice.

Should the concentration of pulp be too high, pressure limits within the pulp pasteurizer may be exceeded as well as proper feeding of the pulp pasteurizer can occur. Often this will create a blockage within the pulp pasteurizer and/or cause the temperatures within the pulp pasteurizer to fall out of specification preventing proper sterilization. This may result in either the loss of product or lower capacity.

Current methods to address these problems involve taking spot samples of the pulp discharge from the pulp concentrator and measuring the pulp concentration. Changes may then be made to the process to correct out of specification feed to the pulp pasteurizer.

One such measurement method is the grams/liter test, where a liter of pulp is mixed with a liter of water and put through a screening device to separate the water from the pulp. The remaining pulp on the screen is then weighed to determine the density.

Another measurement method is the quick fiber analysis, where dryness of the pulp is determined based on the free liquid that is removed without the application of pressure. For example, 200 grams of pulp sample are mixed with about 200 milliliters of water and stirred for a minute. This mixture sits for three minutes and is then stirred for another minute. The mixture is placed into a shaker with a 40 mesh screen for about three minutes and the liquid is retrieved from the sample. The liquid is measured in a graduated cylinder where the amount of liquid measured (in milliliters) is called the quick fiber. The total time is about 8-10 minutes, with even more time being needed for preparation.

As an alternative to the grams/liter test and the quick fiber analysis, pulp concentration may be measured using a nuclear magnetic resonance (NMR) sensor. U.S. Pat. No. 6,375,996, assigned to the present assignee, the disclosure of which is hereby incorporated by reference in its entirety, discloses obtaining a sample of the pulp, and measuring the pulp dryness using an NMR sensor.

Based on pulp concentrations in the sample measurements, manual adjustments may then be made to the pulp concentrator. In a screw type finisher, pulp concentration is changed by adjusting the finisher air pressure. In a paddle finisher, pulp concentration is changed by varying the speed of the paddle.

A disadvantage of performing the above described sample measurement approaches is that over time there may be wide variances in the pulp concentrations that can change even as pulp is being sampled and analyzed.

SUMMARY OF THE INVENTION

In view of the foregoing background, it is therefore an object of the present invention to sense and control pulp concentration within a concentrated pulp stream output from a pulp concentrator.

This and other objects, features, and advantages in accordance with the present invention are provided by a juice processing apparatus comprising a concentrator for generating at least one concentrated pulp stream, a pulp pasteurizer coupled downstream from the concentrator, and a flow restrictor coupled in the at least one concentrated pulp stream for generating a pressure drop therein. The pressure drop may be indicative of a concentration of pulp in the at least one concentrated pulp stream. At least one pressure sensor may be associated with the flow restrictor for sensing the pressure drop. A controller may be for controlling the concentrator based upon the sensed pressure drop.

The juice processing apparatus advantageously allows for the continuous sensing of the pulp concentration in the at least one concentrated pulp stream. The controller may then control the concentrator to maintain a pulp concentration in the at least one concentrated pulp stream within a predetermined range regardless of upstream process variations which might otherwise cause wide variations in pulp density discharged by the concentrator.

The flow restrictor may comprise a tube having an inlet and an outlet, for example. The at least one pressure sensor may comprise an inlet pressure sensor associated with the inlet, and an outlet pressure sensor associated with the outlet.

The at least one concentrated pulp stream may comprise a primary concentrated pulp stream and a secondary concentrated pulp stream both having a same pulp concentration. The primary concentrated pulp stream may have a higher flow rate than the secondary concentrated pulp stream. The flow restrictor may be in the secondary concentrated pulp stream.

The juice processing apparatus may further comprise at least one fluid pump coupled between the concentrator and the flow restrictor to maintain the secondary concentrated pulp stream at a predetermined flow rate. The juice processing apparatus may further comprise at least one flow rate sensor in the secondary concentrated pulp stream to measure the flow rate.

The juice processing apparatus may further comprise a raw juice source upstream of the concentrator. The concentrator may further generate a juice stream for a juice pasteurizer downstream from the concentrator.

Another aspect is directed to a pulp concentration sensing and control assembly for a juice processing apparatus comprising a concentrator for generating at least one concentrated pulp stream, and a pulp pasteurizer coupled downstream from the concentrator. The pulp concentration sensing and control assembly may comprise a flow restrictor to be coupled in the at least one concentrated pulp stream for generating a pressure drop therein, with the pressure drop being indicative of a concentration of pulp in the at least one concentrated pulp stream. At least one pressure sensor may be associated with the flow restrictor for sensing the pressure drop. A controller may be for controlling the concentrator based upon the sensed pressure drop.

Yet another aspect is directed to a method for sensing and controlling pulp concentration for a juice processing apparatus as described above. The method may comprise generating a pressure drop in a flow restrictor coupled in the at least one concentrated pulp stream, with the pressure drop being indicative of a concentration of pulp in the at least one concentrated pulp stream. The pressure drop may be sensed using at least one pressure sensor associated with the flow restrictor, and the controller may be operated for controlling the concentrator based upon the sensed pressure drop.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
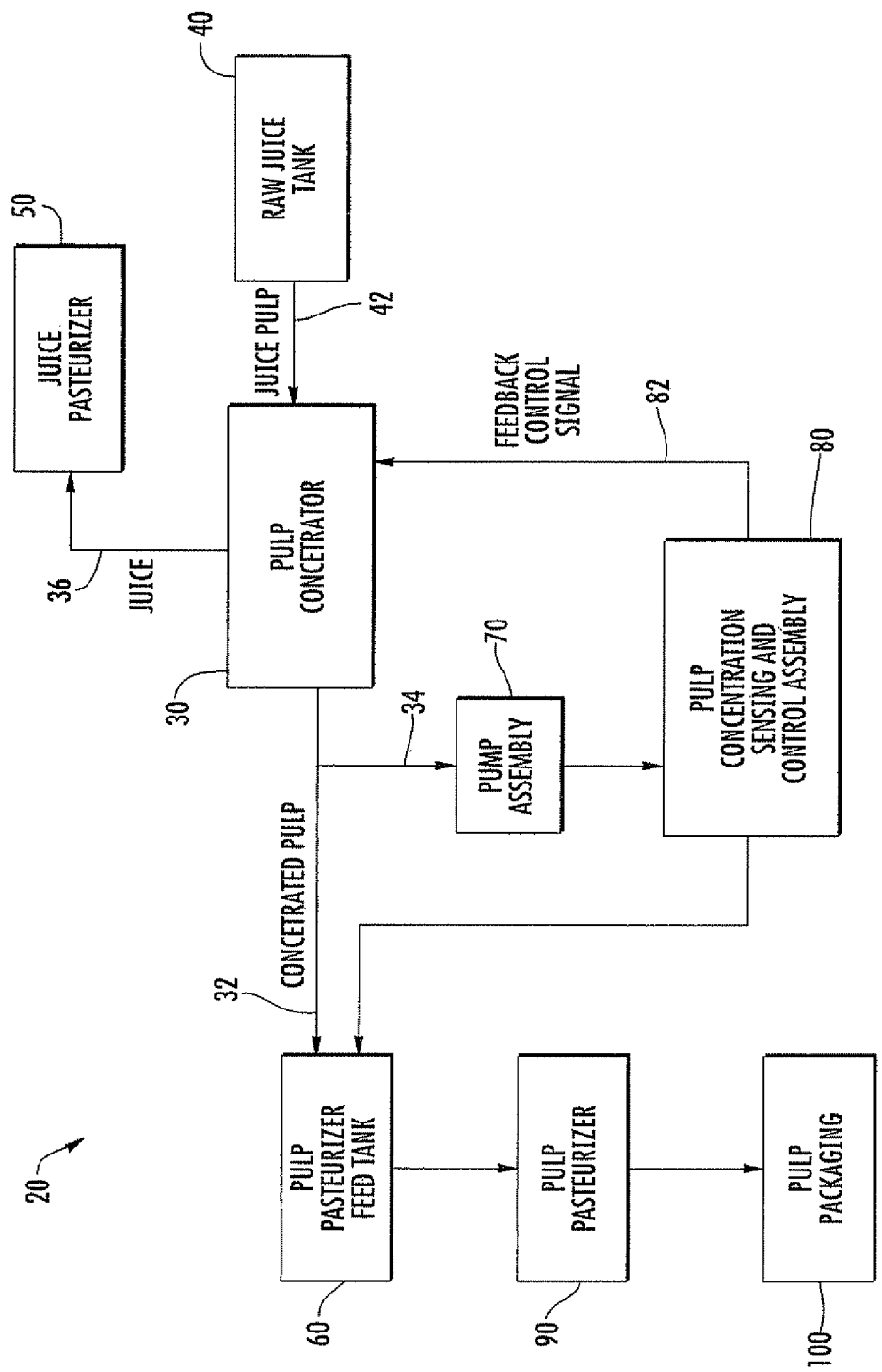
FIG. 1 is a block diagram of a juice processing apparatus in accordance with the present invention.

Referring initially to FIG. 1, a juice processing apparatus 20 includes a pulp concentrator 30 that is fed from a raw juice tank 40. The pulp concentrator 30 is also known as a finisher, which may include either a screw type finisher and/or a paddle finisher. The raw juice tank 40 provides a stream 42 of liquid juice and pulp to the pulp concentrator 30. Although not illustrated, an extractor is used to feed the raw juice tank 40 by extracting the liquid juice and pulp from fruit, such as an orange, or a vegetable.

The pulp concentrator 30 generates a primary concentrated pulp stream 32, a secondary concentrated pulp stream 34, and a juice stream 36. The juice stream 36 is fed to a juice pasteurizer 50. The primary concentrated pulp stream 32 is fed to a pulp pasteurizer feed tank 60. The secondary concentrated pulp stream 34 is fed to a pump assembly 70 and a pulp concentration sensing and control assembly 80 before being also fed to the pulp pasteurizer feed tank 60.

As will be discussed in greater detail below, the pump assembly 70 and the pulp concentration sensing and control assembly 80 advantageously allows for a continuous sensing of the pulp concentration of the secondary concentrated pulp stream 34 as it is discharged from the pulp concentrator 30.

The primary concentrated pulp stream 32 and the secondary concentrated pulp stream 34 both have the same pulp concentration. The primary concentrated pulp stream 32 has a higher flow rate than the secondary concentrated pulp stream 34. The secondary concentrated pulp stream 34 may be referred to as a slip stream sample of the primary concentrated pulp stream 32. The primary and secondary concentrated pulp streams 32, 34 are typically measured in gallons/minute. A flow rate of the secondary concentrated pulp stream 34 is typically within a range of about 5-25% of the flow rate of the primary concentrated pulp stream 32.

Feedback information from the pulp concentration sensing and control assembly 80 is provided to the pulp concentrator 30. Based on measured variations of the pulp concentration within the secondary concentrated pulp stream 34, the pulp concentration sensing and control assembly 80 automatically provides a varying feedback output signal 82 to the pulp concentrator 30 so that a desired pulp concentration, typically in grams per liter, can be maintained regardless of upstream process variations which might otherwise cause wide variations in pulp density discharged by the juice concentrator 30. The pulp concentration sensing and control assembly 80 enables the user to define a desired pulp concentration which maximizes production, and prevents process upsets within the downstream pulp pasteurizer 90 being fed by the pulp pasteurizer feed tank 60.

The pulp concentration sensing and control assembly 80 compares the desired set point to that of the measured value and provides the feedback control signal 82 to the pulp concentrator 30 to increase or decrease the density of the discharged pulp stream. For example, if the pulp concentrator 30 includes a screw type finisher, pulp concentration is changed by adjusting the finisher air pressure as readily understood by those skilled in the art. Similarly, if the pulp concentrator 30 includes a paddle finisher, pulp concentration is changed by varying the speed of the paddle as also readily understood by those skilled in the art.

In the event that the pulp concentration sensing and control assembly 80 cannot produce the desired concentration of pulp, preset alarms are generated allowing the user to take immediate steps to correct the situation prior to producing either a failure within the pulp pasteurizer 90, such as plugging, or the production of an out-of-specification product at the pulp packaging 100 downstream from the pulp pasteurizer 90.

An additional feature is to allow for the user to acquire information via a network connection as to the concentration of pulp which has been fed to the pulp pasteurizer 90. In the cases where no additional juice is separated prior to packaging, this information provides for validation and documentation of the pulp density at the pulp packaging 100.

Figure 2:
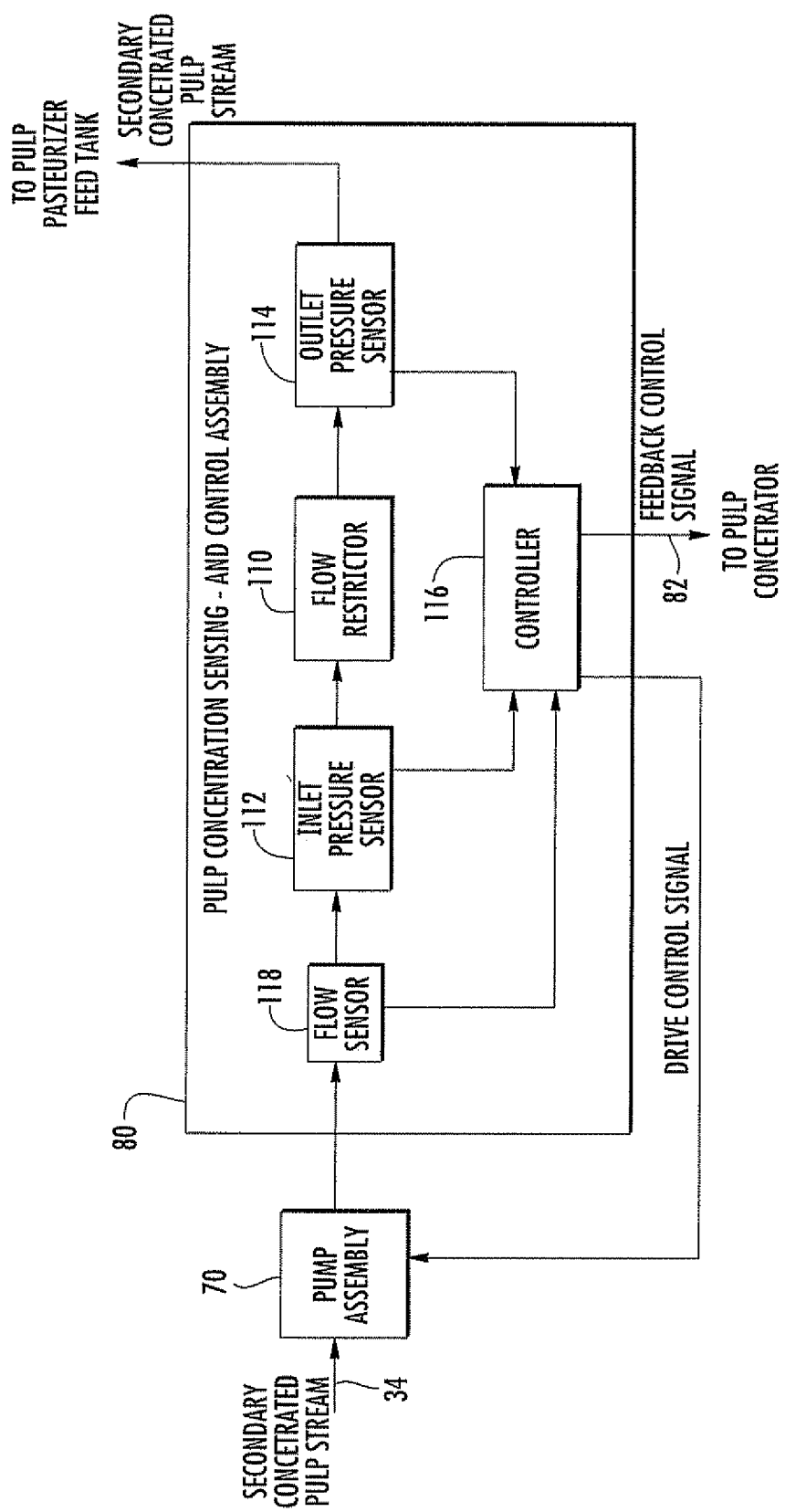
FIG. 2 is a detailed block diagram of the pulp concentration sensing and control assembly shown in FIG. 1.

Referring now to FIG. 2, the pulp concentration sensing and control assembly 80 will now be discussed in greater detail. In addition, the pump assembly 70 will also be discussed in greater detail since it is necessary for the pump assembly 70 to provide the secondary concentrated pulp stream 34 to the pulp concentration sensing and control assembly 80 at a predetermined flow rate.

The pump assembly 70 comprises a positive displacement pump designed to provide a minimum of shear to the pulp as possible. A typical style for this pump would be a progressive cavity pump.

The pulp concentration sensing and control assembly 80 includes a flow restrictor 110 coupled in the secondary concentrated pulp stream 34 for generating a pressure drop therein, with the pressure drop being indicative of a concentration of pulp in the secondary concentrated pulp stream 34.

As discussed above, the concentration of pulp in the secondary concentrated pulp stream 34 is equal to the concentration of pulp in the primary concentrated pulp stream 32. Pressure sensors 112, 114 are associated with the flow restrictor 110 for sensing the pressure drop. A controller 116 is for controlling the pulp concentrator 30 based upon the sensed pressure drop.

For the pulp concentration sensing and control assembly 80 to operate correctly the pump assembly 70 needs to provide a stream of pulp at a consistent flow rate. In other words, control of the rate at which the secondary concentrated pulp stream 34 is fed into the flow restrictor 110 is important to sensing and controlling the pulp concentration. This control is provided using a flow rate sensor 118 in the secondary concentrated pulp stream 34.

The flow rate sensor 118 provides a flow rate signal to the controller 116 corresponding to the measured flow rate of the secondary concentrated pulp stream 34. In response, the controller 116 generates a drive control signal for a variable speed drive that controls an electrical motor associated with the pump assembly 70, thus maintaining the desired flow rate to the flow restrictor 110. This is necessary for proper sensing of the pulp density in the secondary concentrated pulp stream 34.

The flow restrictor 110 may comprise a tube or venturi tube, for example. The tube 110 has an inlet and an outlet. The length and diameter of the tube 110 is selected to correspond to a consistent and desired pressure drop. In other words, the diameter of the tube 110 is less than the diameter of the pipe feeding the secondary concentrated pulp stream 34 thereto. For example, the diameter of the tube 110 may be within a range of ¼ to ½ inches outside diameter, whereas the diameter of the pipe feeding the secondary concentrated pulp stream 34 thereto may be within a range of 1 to 2 inches outside diameter. The length of the tube 110 may also vary, but a typical length may be within a range of about 6 to 18 inches, for example. Other lengths and diameters may be used as long as a consistent and desired pressure drop is maintained across the tube 110.

The desired pressure drop across the tube 110 is based on the characteristics of pulp at the desired concentration range of the downstream pulp pasteurizer 90. The inlet pressure sensor 112 is associated with the inlet of the tube 110, and measures the pressure prior to entering the flow restrictor. The outlet pressure sensor 114 is associated with the outlet of the tube 110, and measures the pressure exiting the flow restrictor. The outlet pressure sensor 114 is intended to isolate the effects of pressure losses created by the pulpy stream as it exits the flow restrictor.

The controller 116 receives pressure signals from the inlet and outlet pressure sensors 112, 114. The controller 116 executes an algorithm that incorporates the known characteristic of the flow restrictor 110 as it reacts (i.e., pressure drop) to variances of pulp concentration and the flow rate of the secondary concentrated pulp stream 34 provided thereto.

The algorithm calculates the pulp concentration and produces and averages this over time, and then generates the feedback control signal 82 for control of the pulp concentrator 30 based on the average measured values and the desired pulp concentration as set by the user. The feedback control signal 82 is not limited to a single signal, but could include two or more signals.

Figure 3:
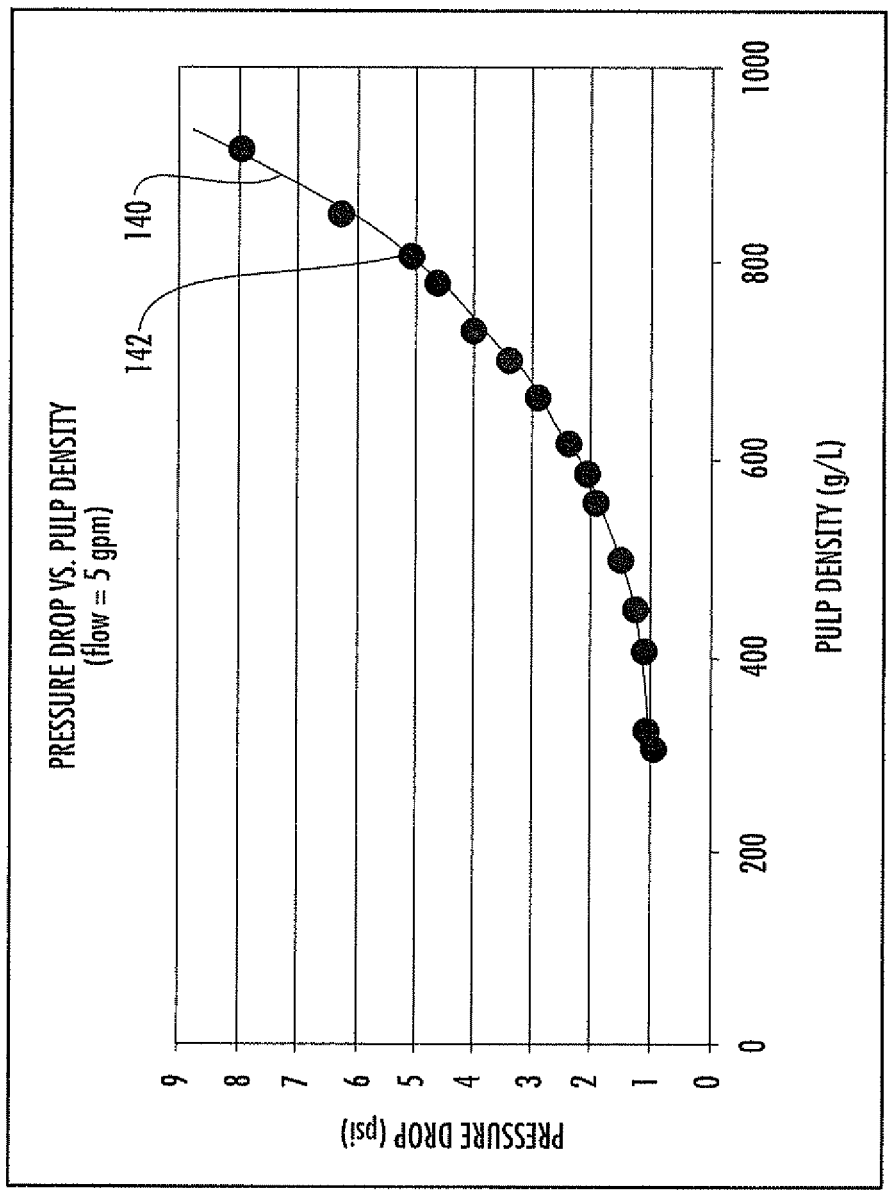
FIG. 3 is a graph illustrating pressure drop versus pulp density in accordance with the present invention.

As illustrated in FIG. 3, pressure drop versus pulp density is plotted along line 140 for a uniform flow rate through the flow restrictor 110. The horizontal axis is the pulp density in grams per liter (g/l), and the vertical axis is pressure drop in pounds per square inch (psi). The flow rate of the secondary concentrated pulp stream 34 received by the flow restrictor 110 is 5 gallons per minute (gpm).

For example, a pressure drop of 5 psi corresponds to a pulp concentration of 800 g/l for a flow rate of 5 gpm, as indicated by point 142. Test data will vary based the size (length and diameter) of the flow restrictor 100, and the flow rate of the secondary concentrated pulp stream 34, as readily appreciated by those skilled in the art.

The pulp concentration at the output of the pulp concentrator 30 may thus be determined by comparing the pressure drop at a given flow rate across the flow restrictor 110 to previously collected empirical data, such as shown in FIG. 3. The controller 116 also includes a user interface that allows the user to input a pulp concentration set point. This set point may be entered locally at the user interface or remotely via network connection.

To maintain pulp concentration from the pulp concentrator 30 within a narrow user-defined band, the controller 116 may compare the measured pressure drop across the flow restrictor 110 to the set point from the user interface. The set point may either be entered as a unit of pressure drop, for example pounds per square inch, or may a unit of pulp density, for example grams per liter. If the set point is entered as a unit of pulp density, the controller 116 may convert the pulp density set point to a pressure drop set point based on previously collected empirical data. If the measured pressure drop across the controller 116 is different than the user-defined set point, the controller will send a signal to the pulp concentrator 30 to either increase or decrease pulp density. The controller 116 may contain an algorithm to control pulp concentration versus a desired set point. The controller 116 may also provide an alarm if the measured pulp density deviates from the set point, or if the controller 116 is not able to achieve the set concentration within a given period of time. The controller 116 may also record historical set points and measured pulp density data to allow the user to review historical performance.

Figure 4:
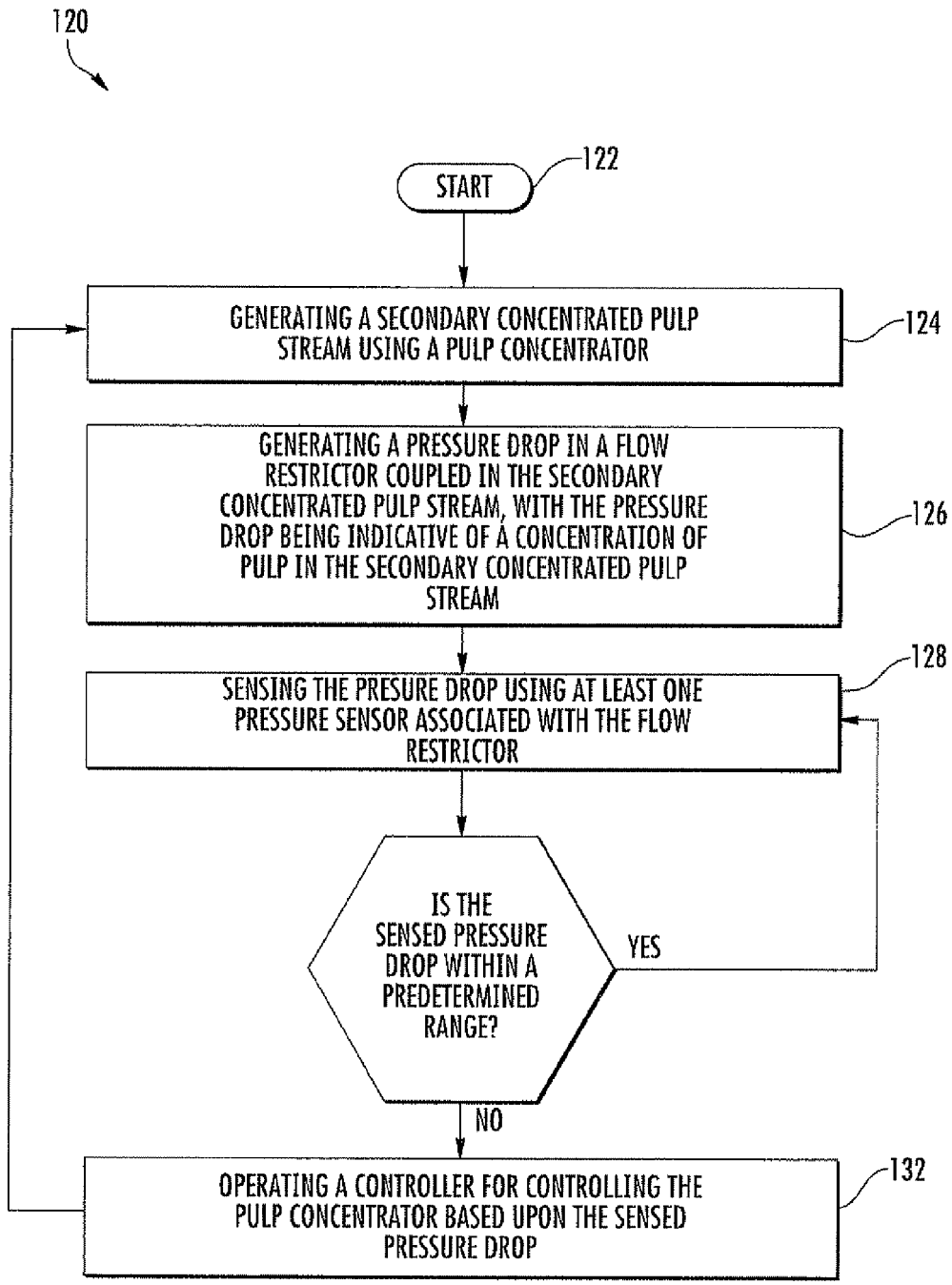
FIG. 4 is a flowchart illustrating a method for sensing and controlling pulp concentration for a juice processing apparatus in accordance with the present invention.

Another aspect is directed to a method for sensing and controlling pulp concentration for a juice processing apparatus 20 as described above. Referring now to the flowchart 120 in FIG. 4, from the start (Block 122), the method comprises generating a secondary concentrated pulp stream 34 using a pulp concentrator 30 at Block 124. At Block 126, a pressure drop is generated in a flow restrictor 110 coupled in the secondary concentrated pulp stream 34. The pressure drop is indicative of a concentration of pulp in the secondary concentrated pulp stream 34. The pressure drop is sensed using at least one pressure sensor 112, 114 associated with the flow restrictor 110 at Block 128. At decision block 130, the sensed pressure drop is compared to a predetermined range. If the sensed pressure drop is within the predetermined range, then the pressure drop is continued to be sensed at Block 128. However, if the sensed pressure drop is not within the predetermined range, then the method comprises operating a controller 116 at Block 132 for controlling the pulp concentrator 30 based upon the sensed pressure drop at Block 128. The controller generates a feedback control signal 82 for the pulp concentrator.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A juice processing apparatus comprising:
   a concentrator for generating at least one concentrated fruit or vegetable pulp stream;
   a flow restrictor coupled in the at least one concentrated fruit or vegetable pulp stream for generating a pressure drop therein, the pressure drop being indicative of a concentration of fruit or vegetable pulp in the at least one concentrated fruit or vegetable pulp stream, said flow restrictor comprising a tube having an inlet and an outlet;
   at least one pressure sensor coupled to said flow restrictor for sensing the pressure drop, said at least one pressure sensor comprising an inlet pressure sensor coupled to the inlet; and
   a controller for controlling said concentrator based upon the sensed pressure drop.

2. The juice processing apparatus according to claim 1 further comprises a fruit or vegetable pulp pasteurizer coupled downstream from said concentrator.

3. The juice processing apparatus according to claim 1 wherein said controller is for controlling said concentrator to maintain a fruit or vegetable pulp concentration in the at least one concentrated fruit or vegetable pulp stream within a predetermined range.

4. The juice processing apparatus according to claim 1 wherein said tube comprises a venturi tube.

5. The juice processing apparatus according to claim 1 wherein said at least one pressure sensor further comprises an outlet pressure sensor coupled to the outlet.

6. The juice processing apparatus according to claim 1 wherein the at least one concentrated fruit or vegetable pulp stream comprises a primary concentrated fruit or vegetable pulp stream and a secondary concentrated fruit or vegetable pulp stream both having a same fruit or vegetable pulp concentration; and wherein said flow restrictor is in the secondary concentrated fruit or vegetable pulp stream.

7. The juice processing apparatus according to claim 6 wherein the primary concentrated fruit or vegetable pulp stream has a higher flow rate than the secondary concentrated fruit or vegetable pulp stream.

8. The juice processing apparatus according to claim 1 further comprising a raw juice source upstream of said concentrator.

9. The juice processing apparatus according to claim 8 wherein said concentrator further generates a juice stream.

10. The juice processing apparatus according to claim 9 further comprising a juice pasteurizer downstream from said concentrator.

11. The juice processing apparatus according to claim 1 further comprising at least one fluid pump coupled between said concentrator and said flow restrictor.

12. The juice processing apparatus according to claim 1 further comprising at least one flow rate sensor in the at least one concentrated fruit or vegetable pulp stream.

13. A fruit or vegetable pulp concentration sensing and control assembly for a juice processing apparatus comprising a concentrator for generating at least one concentrated fruit or vegetable pulp stream, the fruit or vegetable pulp concentration sensing and control assembly comprising:
   a flow restrictor to be coupled in the at least one concentrated fruit or vegetable pulp stream for generating a pressure drop therein, the pressure drop being indicative of a concentration of fruit or vegetable pulp in the at least one concentrated fruit or vegetable pulp stream, said flow restrictor comprising a tube having an inlet and an outlet;
   at least one pressure sensor coupled to said flow restrictor for sensing the pressure drop, said at least one pressure sensor comprising an inlet pressure sensor coupled to the inlet; and
   a controller for controlling the concentrator based upon the sensed pressure drop.

14. The fruit or vegetable pulp concentration sensing and control assembly according to claim 13 wherein said controller is for controlling the concentrator to maintain a fruit or vegetable pulp concentration in the at least one concentrated fruit or vegetable pulp stream within a predetermined range.

15. The fruit or vegetable pulp concentration sensing and control assembly according to claim 13 wherein said tube comprises a venturi tube.

16. The fruit or vegetable pulp concentration sensing and control assembly according to claim 13 wherein said at least one pressure sensor further comprises an outlet pressure sensor coupled to the outlet.

17. The fruit or vegetable pulp concentration sensing and control assembly according to claim 13 wherein the at least one concentrated fruit or vegetable pulp stream comprises a primary concentrated fruit or vegetable pulp stream and a secondary concentrated fruit or vegetable pulp stream both having a same fruit or vegetable pulp concentration; and wherein said flow restrictor is in the secondary concentrated fruit or vegetable pulp stream.

18. The fruit or vegetable pulp concentration sensing and control assembly according to claim 17 wherein the primary concentrated fruit or vegetable pulp stream has a higher flow rate than the secondary concentrated fruit or vegetable pulp stream.

19. The fruit or vegetable pulp concentration sensing and control assembly according to claim 13 further comprising at least one fluid pump coupled between said concentrator and said flow restrictor.

20. The fruit or vegetable pulp concentration sensing and control assembly according to claim 13 further comprising at least one flow rate sensor in the at least one concentrated fruit or vegetable pulp stream.

* * * * *